United States Patent
Souza et al.

(10) Patent No.: US 10,858,346 B2
(45) Date of Patent: Dec. 8, 2020

(54) CRYSTALLINE FORM OF LUMACAFTOR

(71) Applicant: Apotex Inc., Toronto (CA)

(72) Inventors: Fabio E. S. Souza, Mississauga (CA); Bahareh Khalili, Mississauga (CA); Katherine A. Rantanen, Burlington (CA)

(73) Assignee: Apotex Inc., Toronto (CA)

( * ) Notice: Subject to any disclaimer, the term of this patent is extended or adjusted under 35 U.S.C. 154(b) by 0 days.

(21) Appl. No.: 16/159,791

(22) Filed: Oct. 15, 2018

(65) Prior Publication Data

US 2019/0112299 A1    Apr. 18, 2019

Related U.S. Application Data

(60) Provisional application No. 62/573,368, filed on Oct. 17, 2017.

(51) Int. Cl.
| | | |
|---|---|---|
| *C07D 405/12* | (2006.01) | |
| *C07D 213/56* | (2006.01) | |
| *A61K 31/47* | (2006.01) | |

(52) U.S. Cl.
CPC ......... *C07D 405/12* (2013.01); *C07D 213/56* (2013.01); *A61K 31/47* (2013.01); *A61K 2300/00* (2013.01)

(58) Field of Classification Search
CPC ............................ C07D 405/12; C07D 213/56
See application file for complete search history.

(56) References Cited

U.S. PATENT DOCUMENTS

| | | | |
|---|---|---|---|
| 8,507,534 B2 * | 8/2013 | Keshavarz-Shokri | ...................... C07D 405/12 514/338 |
| 9,216,969 B2 | 12/2015 | Ruah et al. | |
| 9,314,455 B2 | 4/2016 | Keshavarz-Shokri et al. | |
| 9,840,499 B2 | 12/2017 | Keshavarz-Shokri et al. | |

FOREIGN PATENT DOCUMENTS

| | | | | |
|---|---|---|---|---|
| EP | 3204358 B1 * | 9/2018 | ........... A61K 31/225 |
| WO | 2007056341 A1 | 5/2007 | |
| WO | 2009073757 A1 | 6/2009 | |
| WO | 2011127290 A2 | 10/2011 | |
| WO | 2017025045 A1 | 2/2017 | |
| WO | 2017056109 A2 | 4/2017 | |

OTHER PUBLICATIONS ("Effects of nicotinamide and niacin on bleomycin-induced acute injury and subsequent fibrosis in hamster lungs." Experimental lung research 20.4 (1994): 263-281.*
Bernstein, "Polymorphism in Molecular Crystals", Oxford University Press, New York, 2002, pp. 9-10 ISBN 0198506058.
Remington, "The Science and Practice of Pharmacy 21st Edition", Lippincott Williams & Wilkins: Philadelphia; 2006; Chapter 45, ISBN 0781746736.
Remington, "The Science and Practice of Pharmacy 21st Edition", Lippincott Williams & Wilkins: Philadelphia; 2006; Chapter 47, ISBN 0781746736.

* cited by examiner

*Primary Examiner* — Samira J Jean-Louis
(74) *Attorney, Agent, or Firm* — The Webb Law Firm

(57) ABSTRACT

The present invention provides a novel crystalline form of Lumacaftor, specifically Lumacaftor Form APO-I, a co-crystal of Lumacaftor and nicotinamide, compositions including this crystalline form, and processes for the preparation of this crystalline form.

19 Claims, 1 Drawing Sheet

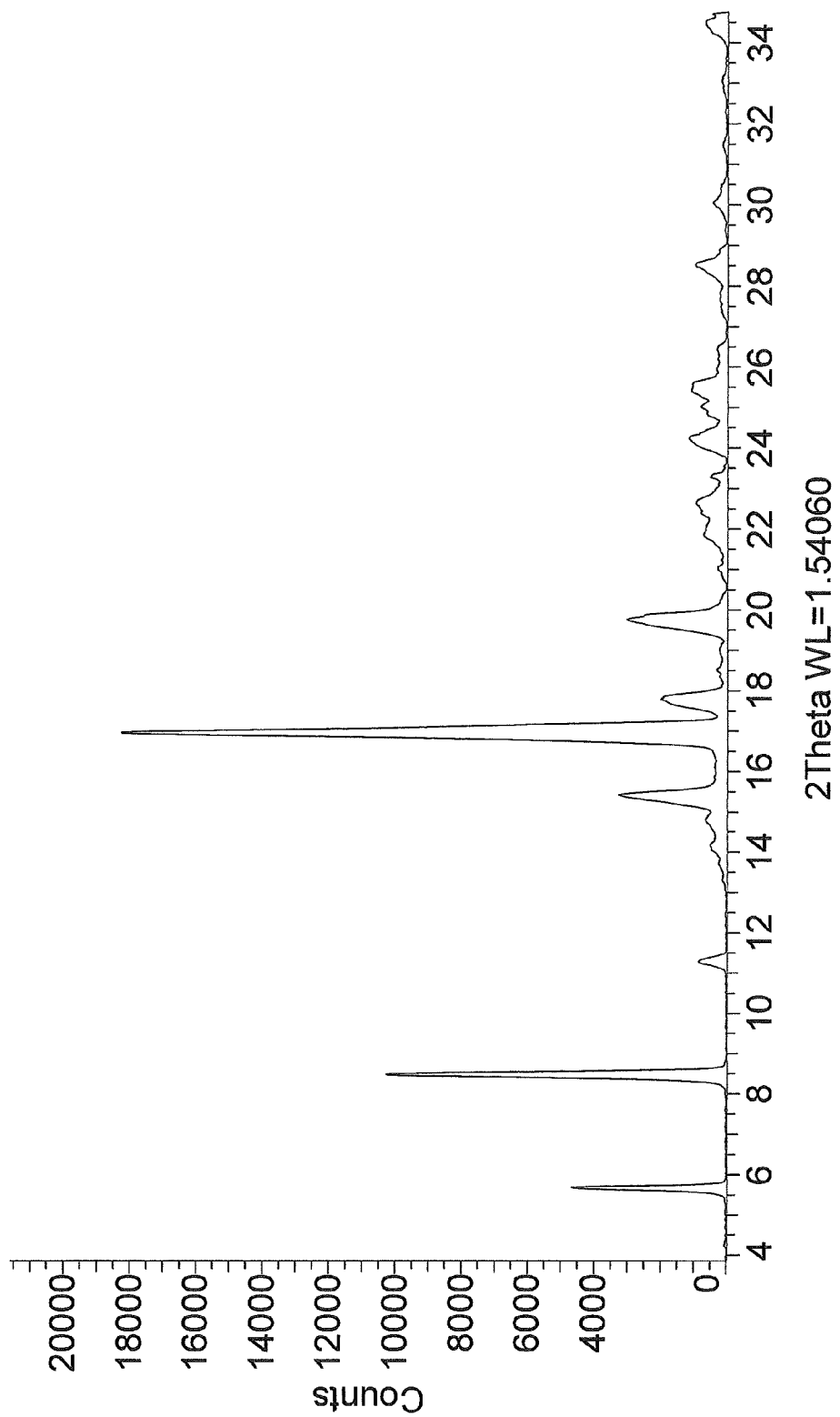

CRYSTALLINE FORM OF LUMACAFTOR

CROSS-REFERENCE TO RELATED APPLICATION

This application claims the benefit of U.S. Provisional Patent Application No. 62/573,368, filed Oct. 17, 2017, the disclosure of which is hereby incorporated in its entirety by reference.

TECHNICAL FIELD

The present invention is directed to a novel crystalline form of Lumacaftor and processes for the preparation thereof.

BACKGROUND

The compound 3-[6-({[1-(2,2-difluoro-1,3-benzodioxol-5-yl)cyclopropyl]carbonyl}amino)-3-methylpyridin-2-yl] benzoic acid (1), commonly known as Lumacaftor, is described in WO 2007/056341 A1. Lumacaftor is marketed in the United States in a fixed dose combination (FDC) tablet with Ivacaftor as ORKAMBI®, and is indicated for the treatment of cystic fibrosis (CF) in patients age 6 years and older who are homozygous for the F508del mutation in the CFTR (cystic fibrosis transmembrane conductance regulator) gene.

(1)

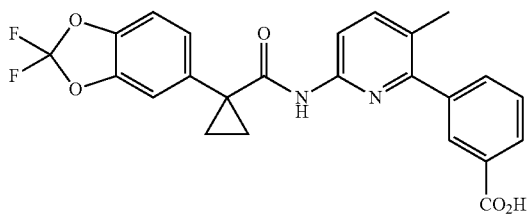

Crystalline forms of Lumacaftor, including solvated forms, are disclosed, for example, in WO 2009/073757 A1, WO 2011/127290 A2, WO 2017/025045 A1, and WO 2017/056109 A2.

According to WO 2011/127290 A2, Lumacaftor forms isostructural solvates in which voids in the crystalline lattice are empty, or occupied or partially occupied by one or more molecules of a solvent such as methanol, ethanol, acetone, 2-propanol, acetonitrile, tetrahydrofuran, methyl acetate, 2-butanone, ethyl formate, or 2-methyl tetrahydrofuran. WO 2017/056109 A2 describes further solvates of Lumacaftor with ethyl acetate and acetic acid. Preparation of non-solvated forms, described in WO 2009/073757 A1 (Form I) and WO 2017/025045 A1 (Form A), involves procedures requiring treatment of either an acid salt or synthetic precursor of Lumacaftor to provide the desired form, or involves evaporating a solution of Lumacaftor at elevated temperature for several days.

Solvated crystalline forms of a pharmaceutical substance can present challenges due to the incorporation of a volatile solvent, which can be subject to displacement during normal drying, handling, storage and formulation activities associated with industrial processing of a drug. Furthermore, the propensity of Lumacaftor specifically to form isostructural solvates having voids that can be empty, or wholly or partially occupied by various solvents, could give rise to questions of regulatory compliance due to the requirement that the characteristics of a pharmaceutical substance be well-defined and controlled. On the other hand, available methods to prepare non-solvated forms, such as Form I and Form A, suffer from either the need to start from an acid salt or synthetic precursor of Lumacaftor, thereby limiting the flexibility of the synthetic approaches that can be used to prepare the molecule, or involve lengthy and inefficient evaporative methods, which are undesirable for application on a commercial scale.

Different crystalline forms of the same compound may have different packing, thermodynamic, spectroscopic, kinetic, surface and mechanical properties. For example, different crystalline forms may have different stability properties. A particular crystalline form may be more sensitive to heat, relative humidity (RH) and/or light. Alternatively or additionally, a particular crystalline form may provide more compressibility and/or density properties thereby providing more desirable characteristics for formulation and/or product manufacturing. Particular crystalline forms may also have different dissolution rates, thereby providing different pharmacokinetic parameters, which allow for specific forms to be used in order to achieve specific pharmacokinetic targets. Additionally, the particular solubility characteristics of a given crystalline form in relation to undesired impurities can result in differences in the chemical purity of different crystalline forms upon isolation. Differences in stability may result from changes in chemical reactivity, such as differential oxidation. Such properties may provide for more suitable product qualities, such as a dosage form that is more resistant to discolouration when comprised of a specific crystalline form. Different physical properties of crystalline forms may also affect their processing. For example, a particular crystalline form may be more resistant to flow, or may be more difficult to filter and/or wash.

Although general approaches to crystalline form screening of active pharmaceutical ingredients are known, it is well established that the prediction of whether any given compound will exhibit polymorphism is not possible. Furthermore, prediction of the properties of any unknown crystalline forms, and how they will differ from other crystalline forms of the same compound, remains even more elusive (Joel Bernstein, *Polymorphism in Molecular Crystals*, Oxford University Press, New York, 2002, page 9).

Therefore, a need exists for a novel crystalline form of Lumacaftor for use in providing improved drug products containing Lumacaftor and their manufacture.

SUMMARY OF THE INVENTION

The Lumacaftor crystalline form of the present invention, which is a co-crystal of Lumacaftor and nicotinamide, exhibits differences in properties when compared to the known crystalline forms of Lumacaftor. Properties that differ between the invention and known crystalline forms of Lumacaftor include the following: packing properties such as molar volume, density and hygroscopicity; thermodynamic properties such as melting and solubility; kinetic properties such as dissolution rate and chemical/polymorphic stability; surface properties such as crystal habit; and/or mechanical properties such as hardness, tensile strength, compactibility, tableting, handling, flow, and blending.

Surprisingly, despite the propensity of Lumacaftor to form solvated crystalline forms with a variety of solvents, the present invention provides a novel crystalline form of Lumacaftor which does not incorporate the preparation solvent as part of a solvated crystalline form. Rather, it has been found that, when Lumacaftor is crystallized in the presence of nicotinamide, a co-crystal will form as opposed to a solvated or non-solvated form of Lumacaftor. Surprisingly, co-crystal formation occurs even when the crystalline form of the present invention is prepared from solvents such as acetone and acetonitrile, which are reported in WO 2011/127290 A2 to form an isostructural solvate with Lumacaftor. This characteristic is beneficial during the drying, handling and storage of the drug substance and the drug product as crystalline forms incorporating solvents may be subject to incidental solvent displacement or loss resulting in polymorphic conversion or degradation. Advantageously, the crystalline form of the present invention resists polymorph conversion following storage at 40° C./75% R.H. (relative humidity) for at least 7 days. The crystalline form of the present invention is also prepared directly from Lumacaftor by an industrially feasible process that is amenable to large-scale batch-type manufacturing, thereby allowing for flexibility in the choice of the synthetic route used for the preparation of Lumacaftor.

In addition, nicotinamide is an essential vitamin and is included in the U.S. Food & Drug Administration's (FDA's) GRAS (Generally Recognized as Safe) list, which is an inventory of substances generally recognized by the FDA as having been adequately shown to be safe under the conditions of intended use.

Accordingly, in a first aspect of the present invention, there is provided a crystalline form of Lumacaftor that is a co-crystal of Lumacaftor and nicotinamide. Preferably, the molar ratio of Lumacaftor to nicotinamide is between approximately 1:1 and 1:3. Even more preferably, the molar ratio of Lumacaftor to nicotinamide is between approximately 1:1.5 and 1:2.5. Most preferably, the molar ratio of Lumacaftor to nicotinamide is approximately 1:2.

In a second aspect of the present invention, there is provided a crystalline form of Lumacaftor, APO-I, that is a co-crystal of Lumacaftor and nicotinamide characterized by a PXRD diffractogram comprising peaks, expressed in degrees 2θ (±) 0.2°, at 5.7°, 8.5° and 17.0°. In a preferred embodiment of the second aspect, the PXRD diffractogram further comprises peaks, expressed in degrees 2θ (±0.2°), at 11.3°, 15.4°, 17.8° and 19.8°. In this second aspect of the invention, the molar ratio of Lumacaftor to nicotinamide is preferably approximately 1:2. In another preferred embodiment of the second aspect, the crystalline form provides a PXRD diffractogram comprising peaks in substantially the same positions (approximately ±0.2° 2θ) as those shown in FIG. 1.

In a third aspect of the present invention, there is provided a process for the preparation of a co-crystal of Lumacaftor and nicotinamide, the process comprising:
(a) combining Lumacaftor and nicotinamide in a solvent to form a mixture;
(b) maintaining the mixture at a suitable temperature followed by a period of cooling, if necessary; and
(c) filtering the resulting suspension to isolate a co-crystal of Lumacaftor and nicotinamide.

In a preferred embodiment of the third aspect, the solvent is selected from acetone, acetonitrile and cyclopropyl methyl ether. Preferably, the solvent is acetone. In another preferred embodiment of the third aspect of the invention, the mixture of Lumacaftor and nicotinamide dissolves in the solvent to provide a solution. In a further preferred embodiment of the third aspect, the suitable temperature is between room temperature and 60° C. In another preferred embodiment of the third aspect, the molar ratio of Lumacaftor to nicotinamide used in the process is at least approximately 1:2, and is more preferably between approximately 1:3 to approximately 1:5. Most preferably, the molar ratio of Lumacaftor to nicotinamide used in the process is approximately 1:4.

In a fourth aspect of the present invention, there is provided a use of a co-crystal of Lumacaftor and nicotinamide in the treatment of cystic fibrosis. In a preferred embodiment of the fourth aspect, the co-crystal of Lumacaftor and nicotinamide is Lumacaftor form APO-I, as described in the second aspect of the invention. In a further preferred embodiment of the fourth aspect, the Lumacaftor co-crystal is used in the treatment of cystic fibrosis patients who are homozygous for the F508del mutation in the CFTR gene. In another further preferred embodiment of the fourth aspect, the Lumacaftor co-crystal is used in combination with Ivacaftor.

In a fifth aspect of the present invention, there is provided a pharmaceutical composition comprising a co-crystal of Lumacaftor according to the first or second aspect, and one or more pharmaceutically acceptable excipients. Preferably, the pharmaceutical composition is in the form of a solid dosage form. Most preferably, the pharmaceutical composition is a tablet or comprises granules. In a preferred embodiment of the fifth aspect, the co-crystal of Lumacaftor and nicotinamide is Lumacaftor form APO-I, as described in the second aspect of the invention. In a further preferred embodiment of the fifth aspect, the pharmaceutical composition further comprises Ivacaftor. More preferably, the pharmaceutical composition is a fixed dose combination comprising Ivacaftor and a co-crystal of Lumacaftor and nicotinamide according to the first or second aspect.

Other aspects and features of the present invention will become apparent to those ordinarily skilled in the art upon review of the following description of specific embodiments of the invention in conjunction with the accompanying figures.

BRIEF DESCRIPTION OF THE DRAWING

Embodiments of the present invention are described, by way of example only, with reference to the attached FIGURE.

FIG. 1 is a representative PXRD diffractogram of Lumacaftor Form APO-I as prepared in Example 1.

DETAILED DESCRIPTION

The Lumacaftor crystalline form of the present invention exhibits differences in properties when compared to the known crystalline forms of Lumacaftor. Properties that differ between the invention and known crystalline forms of Lumacaftor include the following: packing properties such as molar volume, density and hygroscopicity; thermodynamic properties such as melting and solubility; kinetic properties such as dissolution rate and chemical/polymorphic stability; surface properties such as crystal habit; and/or mechanical properties such as hardness, tensile strength, compactibility, tableting, handling, flow, and blending.

Surprisingly, despite the propensity of Lumacaftor to form solvated forms with a variety of solvents, the present invention provides a novel crystalline form of Lumacaftor which does not incorporate the preparation solvent as part of a solvated crystalline form. Rather, it has been found that, when Lumacaftor is crystallized in the presence of nicotinamide, a co-crystal will form as opposed to a solvated or non-solvated form of Lumacaftor. Surprisingly, co-crystal formation occurs even when the crystalline form of the present invention is prepared from solvents such as acetone and acetonitrile, which are reported in WO 2011/127290 A2 to form an isostructural solvate with Lumacaftor. This characteristic is beneficial during the drying, handling and storage of the drug substance and the drug product as crystalline forms incorporating solvents may be more prone to incidental solvent displacement or loss resulting in polymorphic conversion or degradation. Advantageously, the crystalline form of the present invention resists polymorph conversion following storage at 40° C./75% R.H. (relative humidity) for at least 7 days. The crystalline form of the present invention is also prepared directly from Lumacaftor by an industrially feasible process that is amenable to large-scale batch-type manufacturing, thereby allowing for flexibility in the choice of the synthetic route used for the preparation of Lumacaftor.

In addition, nicotinamide is an essential vitamin and is included in the FDA's GRAS list, which is an inventory of substances generally recognized by the FDA as having been adequately shown to be safe under the conditions of intended use.

Depending on the manner in which the embodiments of the invention are prepared, the methodology and instrument used for PXRD analysis, and the scale selected to display results, the intensity of a given peak observed in the PXRD diffractogram may vary when compared to the same peak in the representative PXRD diffractogram provided in FIG. 1 to illustrate the embodiments of the invention provided herein. Thus, differences in relative peak intensities between peaks in a PXRD diffractogram for a given crystalline form may be observed when compared to the relative peak intensities of the peaks in the representative PXRD diffractogram of FIG. 1. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractogram provided in FIG. 1, it is understood that individual peak positions may vary between ±0.2° 2θ from the values observed in the representative PXRD diffractogram provided in FIG. 1 for the crystalline form of the invention, or listed in Table 1. Such variations are known and understood by a person of skill in the art, and any such variations do not depart from the invention disclosed herein.

Further, it is understood that, depending on the instrument used for X-ray analysis and its calibration, uniform offsets in the peak position of each peak in a PXRD diffractogram of greater that 0.2° 2θ may be observed when compared to the representative PXRD diffractogram provided in FIG. 1. Thus, PXRD diffractograms of the crystalline form of the present invention may, in some circumstances, display the same relative peak positions as observed in the representative PXRD diffractogram provided in FIG. 1, with the exception that each peak is offset in the same direction, and by approximately the same amount, such that the overall PXRD diffractogram is substantially the same in appearance as a PXRD diffractogram of FIG. 1, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractogram of FIG. 1 for the crystalline form of the invention.

As used herein, the term 'crystalline form' refers to a substance with a particular arrangement of molecular components in its crystal lattice, and which may be identified by physical characterization methods such as PXRD. As used herein, the term crystalline form is intended to include single-component and multiple-component crystalline forms of Lumacaftor. Single-component forms of Lumacaftor consist solely of Lumacaftor in the repeating unit of the crystal lattice. Multiple-component forms of Lumacaftor include co-crystals, salts and solvates of Lumacaftor wherein a co-former, counterion or solvent is also incorporated into the crystal lattice. In the multiple component crystals of the present invention, a co-former, nicotinamide, is also incorporated into the crystal lattice with Lumacaftor.

As used herein, the term 'co-crystal' refers to a multiple-component crystalline form containing both Lumacaftor and a co-former that is solid under ambient conditions.

Multi-component crystalline form comprising more than one type of molecule, such as co-crystals, may have some variability in the exact molar ratio of their components depending on a variety of conditions used. For example, a molar ratio of components within a multi-component crystalline form provides a person of skill in the art information as to the general relative quantities of the components of the crystalline form. In many cases, the molar ratio may vary by ±20% from a stated range. For example, with respect to the present invention, a molar ratio of 1:2 should be understood to include the ratios 1:1.6 and 1:2.4, as well as all of the individual ratios in between.

As used herein, the term "room temperature" refers to a temperature in the range of 20° C. to 25° C.

Unless defined otherwise herein, the term "approximately", when used in reference to molar ratios, allows for a variance of plus or minus 10%.

As used herein, the terms "wt %" or "% w/w" refer to weight percent and is used to express weight solute/weight solution as a percentage.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In one embodiment of the present invention, there is provided a new crystalline form of Lumacaftor, Lumacaftor Form APO-I, which is a co-crystal of Lumacaftor and nicotinamide. Preferably, in Lumacaftor Form APO-I, the molar ratio of Lumacaftor to nicotinamide is approximately 1:2.

Lumacaftor Form APO-I can be characterized by a PXRD diffractogram comprising, among other peaks, characteristic peaks, expressed in degrees 2θ (±0.2°), at 5.7°, 8.5° and 17.0°. Preferably, the PXRD diffractogram further comprises peaks, expressed in degrees 2θ (±0.2°), at 11.3°, 15.4°, 17.8° and 19.8°.

An illustrative PXRD diffractogram of Lumacaftor Form APO-I, as prepared in Example 1, is shown in FIG. 1. A peak listing, comprising representative peaks from the PXRD diffractogram in FIG. 1, and their relative intensities, is provided in Table 1. Although illustrative of the PXRD diffractogram that is provided for the Lumacaftor Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of Lumacaftor Form APO-I from FIG. 1

| Angle (°2θ) | Relative intensity (%) |
|---|---|
| 5.67 | 25.4 |
| 8.47 | 56.2 |
| 11.29 | 4.6 |
| 15.42 | 17.8 |
| 16.95 | 100.0 |
| 17.79 | 10.8 |
| 19.75 | 16.4 |

As described in Example 1, Lumacaftor Form APO-I can be prepared by combining nicotinamide and Lumacaftor in a solvent, preferably acetone, and maintaining the mixture at a suitable temperature, preferably in the range of room temperature to 60° C., followed by a period of cooling, if necessary. Preferably, the mixture dissolves to provide a solution, however, dissolution is not required. Other solvents useful in the procedure are acetonitrile and cyclopentyl methyl ether. The molar ratio of Lumacaftor to nicotinamide used in the procedure is at least approximately 1:2, is preferably between approximately 1:3 and 1:5, and is most preferably approximately 1:4. Filtration of the resulting suspension, and preferably washing with the preparation solvent, provides Lumacaftor Form APO-I having a PXRD diffractogram consistent with FIG. 1.

In a further embodiment of the invention, there is provided a pharmaceutical composition comprising a co-crystal of Lumacaftor and nicotinamide with one or more pharmaceutically acceptable excipients. Preferably, the pharmaceutical composition is a solid dosage form suitable for oral administration, such as a capsule, tablet, pill, powder or granules. Most preferably, the pharmaceutical composition is a tablet or comprises granules.

Suitable pharmaceutically acceptable excipients are preferably inert with respect to the co-crystal of Lumacaftor and nicotinamide, and may include, for example, one or more excipients selected from fillers (for example, starches, lactose, sucrose, glucose, mannitol and silicic acid), binders (for example, carboxymethylcellulose, alginates, gelatin, polyvinylpyrrolidone, sucrose, and acacia), humectants (for example, glycerol), disintegrants (for example, agar, calcium carbonate, potato or tapioca starch, alginic acid, silicates, and sodium carbonate), solution retarding agents (for example, paraffin), absorption accelerators (for example quaternary ammonium compounds), wetting agents (for example, cetyl alcohol and glycerol monostearate), absorbents (for example, kaolin and bentonite clay), lubricants (for example, talc, calcium stearate, magnesium stearate, solid polyethylene glycols, and sodium lauryl sulfate) and buffering agents. The preparation of solid oral dosage forms is well known to person of skill in the art, and is described generally, for example, in *Remington The Science and Practice of Pharmacy* 21st Edition (Lippincott Williams & Wilkins: Philadelphia; 2006; Chapter 45).

Optionally, the solid dosage forms may be prepared with coatings and shells, such as enteric coatings and extended release coatings, using standard pharmaceutical coatings. Such coatings, and their application, are well known to persons skilled in the art, and are described, for example, in *Remington The Science and Practice of Pharmacy* 21st Edition (Lippincott Williams & Wilkins: Philadelphia; 2006; Chapter 46).

Optionally, pharmaceutical compositions according to the present invention can be prepared with other medicinal ingredients for use in combination therapy. Alternatively, combination therapy using the Lumacaftor co-crystal of the present invention can involve individual pharmaceutical compositions for each medicinal ingredient, which are administered concurrently or sequentially.

Preferably, when used in combination therapy, the co-crystal of Lumacaftor and nicotinamide of the present invention is used in combination with Ivacaftor. Thus, in one embodiment of the present invention, there is provided a pharmaceutical composition comprising a fixed dose combination of a co-crystal of Lumacaftor and nicotinamide with Ivacaftor. Pharmaceutical compositions containing a combination of active ingredients may be prepared in the same manner as described above. Preferably, in such fixed dose combinations, the pharmaceutical composition provides doses of Lumacaftor and Ivacaftor that are equivalent to those found in ORKAMBI® tablets. Thus, a preferred fixed dose combination tablet will comprise 308 mg of a 1:2 co-crystal of Lumacaftor and nicotinamide (providing 200 mg Lumacaftor) and 125 mg Ivacaftor. An additional preferred fixed dose combination tablet will comprise 154 mg of a 1:2 co-crystal of Lumacaftor and nicotinamide (providing 100 mg Lumacaftor) and 125 mg Ivacaftor.

EXAMPLES

The following non-limiting example is illustrative of the aspects and embodiments of the invention described herein.

The Lumacaftor used as a starting material in the following examples was consistent with Form I Lumacaftor, which is reported in WO 2009/073757 A1. However, other polymorphic forms are equally suitable as starting material, provided that they have some solubility in the solvent system used such that dissolution of the initial crystalline form and crystallization of the co-crystal of the present invention occurs over the course of the preparation.

PXRD Analysis:

PXRD diffractograms were recorded on a Bruker D8 Discover powder X-ray diffractometer (Bruker-AXS, Karlsruhe, Germany). The generator was a Micro-focus X-ray source (IMSTube: Cu tube with 1.54184 A) with a voltage of 50 kV and current of 1.00 mA, using a divergence slit of 0.3 mm and collimator of 0.3 mm. For each sample, one frame was collected using a still scan with a Pilatus 3R-100 kA detector at the distance of 154.72 mm from the sample. Raw data were evaluated using the program EVA (Bruker-AXS, Karlsruhe, Germany).

Example 1: Preparation of Lumacaftor Form APO-I

A suspension of Lumacaftor (500 mg, 1.1 mmol) and nicotinamide (540 mg, 4.4 mmol) in acetone (8.5 mL) was heated at 55-60° C. for 2 hours, during which time dissolution of the solid materials occurred. The heating was turned off and the reaction mixture was allowed to cool to room temperature. After approximately 2 hours, the resulting thick slurry was filtered, and the cake washed with acetone (3×1 mL+2 mL). Brief drying using the water aspirator (5 min) afforded Lumacaftor Form APO-1 (626 mg, 81% yield). $^1$H NMR analysis of the solid ($d_6$-DMSO))

showed a molar ratio of Lumacaftor:nicotinamide of approximately 1:2. The PXRD diffractogram of a sample prepared by this method is shown in FIG. 1. Further drying at room temperature in vacuo for 22 hours afforded 595 mg of APO-1 having acetone content of approximately 0.3 wt %.

$^1$H-NMR (d$_6$-DMSO, 300 MHz) δ: 1.12-1.21 (m, 2H), 1.47-1.56 (m, 2H), 2.24 (s, 3H), 7.31-7.42 (m, 2H), 7.46-7.53 (m, 2H), 7.53-7.58 (m, 2H), 7.59 (s, 1H), 7.61 (s, 1H), 7.67-7.77 (m, 2H), 7.88-8.01 (m, 3H), 8.17 (s, 2H), 8.21 (d, 2H, J=8.0 Hz), 8.70 (d, 2H, J=4.6 Hz), 9.01 (s, 1H), 9.04 ppm (d, 2H, J=1.2 Hz) ppm.

What is claimed is:

1. A crystalline form of Lumacaftor that is a co-crystal of Lumacaftor and nicotinamide, wherein the co-crystal is characterized by a PXRD diffractogram comprising peaks, expressed in degrees 2θ (±0.2°), at 5.7°, 8.5° and 17.0°.

2. The co-crystal of claim 1, wherein the molar ratio of Lumacaftor to nicotinamide is between approximately 1:1 and approximately 1:3.

3. The co-crystal of claim 1, wherein the molar ratio of Lumacaftor to nicotinamide is approximately 1:2.

4. The co-crystal of claim 1, further comprising peaks, expressed in degrees 2θ (±0.2°), at 11.3°, 15.4°, 17.8° and 19.8°.

5. The co-crystal of claim 4, wherein the molar ratio of Lumacaftor to nicotinamide is approximately 1:2.

6. The co-crystal of claim 5, providing a PXRD diffractogram comprising peaks in substantially the same positions (approximately ±0.2° 2θ) as those shown in FIG. 1.

7. A process for the preparation of a co-crystal of Lumacaftor and nicotinamide, the process comprising:
 (a) combining Lumacaftor and nicotinamide in a solvent to form a mixture;
 (b) maintaining the mixture at a suitable temperature followed by a period of cooling, if necessary; and
 (c) filtering the resulting suspension to isolate a co-crystal of Lumacaftor and nicotinamide,
 wherein the co-crystal is characterized by a PXRD diffractogram comprising peaks, expressed in degrees 2θ (±0.2°), at 5.7°, 8.5° and 17.0°.

8. The process of claim 7, wherein the solvent is selected from the group consisting of acetone, acetonitrile and cyclopropyl methyl ether.

9. The process of claim 8, wherein the solvent is acetone.

10. The process of claim 7, wherein the mixture of Lumacaftor and nicotinamide dissolves in the solvent to provide a solution.

11. The process of claim 10, wherein the solvent is acetone.

12. The process of claim 7, wherein the suitable temperature is between room temperature and 60° C.

13. The process of claim 7, wherein the molar ratio of Lumacaftor to nicotinamide used is at least approximately 1:2.

14. The process of claim 7 wherein the molar ratio of Lumacaftor to nicotinamide used is between approximately 1:3 and approximately 1:5.

15. The process of claim 14, wherein the molar ratio of Lumacaftor to nicotinamide used is approximately 1:4.

16. A pharmaceutical composition comprising the co-crystal according to claim 1, and one or more pharmaceutically acceptable excipients.

17. The pharmaceutical composition of claim 16, wherein the pharmaceutical composition is a tablet.

18. The pharmaceutical composition of claim 16, wherein the pharmaceutical composition comprises granules.

19. The pharmaceutical composition of claim 16, further comprising Ivacaftor.

\* \* \* \* \*